(12) United States Patent
Mastrorio et al.

(10) Patent No.: US 6,363,273 B1
(45) Date of Patent: Mar. 26, 2002

(54) INTRODUCER ELEMENT AND METHOD OF USING SAME

(75) Inventors: Brooke W. Mastrorio, Lakeville; Michael C. Gorhan, South Easton; Timothy A. Beardsley, Kingston, all of MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

(21) Appl. No.: 09/470,062

(22) Filed: Dec. 22, 1999

(51) Int. Cl.[7] ............................ A61B 6/00; A61M 25/00
(52) U.S. Cl. ........................ 600/434; 604/161
(58) Field of Search ............................ 600/435, 434, 600/561, 585; 604/161, 163, 164, 175, 905

(56) References Cited

U.S. PATENT DOCUMENTS

| | | | |
|---|---|---|---|
| 3,669,094 A | 6/1972 | Heyer | 128/2 |
| 4,186,728 A | 2/1980 | van Lotringen | 128/1 R |
| 4,205,675 A | 6/1980 | Vaillancourt | 128/214.4 |
| 4,224,699 A | 9/1980 | Weber | 3/1.913 |
| 4,224,943 A | 9/1980 | Johnson et al. | 128/214.4 |
| 4,270,535 A | 6/1981 | Bogue et al. | 128/214.4 |
| 4,304,231 A | 12/1981 | Bodicky et al. | 128/214.4 |
| 4,306,562 A | 12/1981 | Osborne | 128/348 |
| 4,354,506 A | 10/1982 | Sakaguchi et al. | 128/748 |
| 4,402,685 A | 9/1983 | Bühler et al. | 604/280 |
| 4,412,832 A | 11/1983 | Kling et al. | 604/164 |
| 4,468,224 A | 8/1984 | Enzmann et al. | 604/247 |
| 4,572,212 A | 2/1986 | Letterio | 128/748 |
| 4,581,025 A | 4/1986 | Timmermans | 604/264 |
| 4,613,324 A | 9/1986 | Ghajar | 604/49 |
| 4,629,451 A | 12/1986 | Winters et al. | 604/175 |
| 4,646,752 A | 3/1987 | Swann et al. | 128/748 |
| 4,650,473 A | 3/1987 | Bartholomew et al. | 604/174 |

(List continued on next page.)

FOREIGN PATENT DOCUMENTS

| | | | | |
|---|---|---|---|---|
| EP | 0485118 A1 | 10/1991 | | A61B/5/00 |
| WO | WO97/42870 | 11/1997 | | A61B/5/03 |

*Primary Examiner*—Robert L. Nasser
*Assistant Examiner*—Charles Marmor, II
(74) *Attorney, Agent, or Firm*—Nutter, McClennen & Fish, LLP (57) ABSTRACT

The present invention provides an introducer element for facilitating the insertion of a medical instrument into a body. The introducer element includes first, second, third and fourth housing areas. The first area contains a first lumen and the second area contains a second lumen. A quantity of peel-away tubing is partially disposed within the second lumen. The first and second lumen are separated from each other in the first and second housing areas, but are merged into one lumen in either the third or fourth housing area by a guide/splitting tube.

14 Claims, 9 Drawing Sheets

U.S. PATENT DOCUMENTS

| | | | | |
|---|---|---|---|---|
| 4,676,782 A | | 6/1987 | Yamamoto et al. | 604/175 |
| 4,781,690 A | | 11/1988 | Ishida et al. | 604/164 |
| 4,795,434 A | | 1/1989 | Kujawski | 604/159 |
| 4,805,634 A | | 2/1989 | Ullrich et al. | 128/748 |
| 4,808,157 A | | 2/1989 | Coombs | 604/44 |
| 4,821,716 A | | 4/1989 | Ghajar et al. | 128/303 B |
| 4,865,593 A | | 9/1989 | Ogawa et al. | 604/264 |
| 4,883,468 A | | 11/1989 | Kousai et al. | 604/164 |
| 4,903,707 A | | 2/1990 | Knute et al. | 128/748 |
| 4,931,056 A | | 6/1990 | Ghajar et al. | 606/130 |
| 4,993,425 A | | 2/1991 | Kronberg | 128/748 |
| 4,998,938 A | | 3/1991 | Ghajar et al. | 606/130 |
| 5,007,902 A | | 4/1991 | Witt | 604/117 |
| 5,054,497 A | | 10/1991 | Kapp et al. | 128/748 |
| 5,104,388 A | | 4/1992 | Quackenbush | 604/264 |
| 5,112,309 A | * | 5/1992 | Bertaud et al. | 604/171 |
| 5,116,345 A | | 5/1992 | Jewell et al. | 606/130 |
| 5,163,911 A | * | 11/1992 | Sirimanne et al. | 600/585 |
| 5,168,873 A | | 12/1992 | Seifert et al. | 128/634 |
| 5,190,528 A | | 3/1993 | Fonger et al. | 604/171 |
| 5,207,648 A | | 5/1993 | Gross | 604/164 |
| 5,219,335 A | | 6/1993 | Willard et al. | 604/164 |
| 5,221,263 A | | 6/1993 | Sinko et al. | 604/161 |
| 5,228,452 A | * | 7/1993 | Samson | 600/585 |
| 5,236,424 A | | 8/1993 | Imran | 604/280 |
| 5,250,033 A | | 10/1993 | Evans et al. | 604/160 |
| 5,250,038 A | | 10/1993 | Melker et al. | 604/264 |
| 5,256,149 A | | 10/1993 | Banik et al. | 604/164 |
| 5,281,204 A | | 1/1994 | Horie et al. | 604/164 |
| 5,284,138 A | | 2/1994 | Kujawski | 128/634 |
| 5,290,241 A | * | 3/1994 | Kraus et al. | 604/161 |
| 5,295,968 A | | 3/1994 | Martel et al. | 604/164 |
| 5,306,259 A | | 4/1994 | Fischell et al. | 604/239 |
| 5,312,355 A | | 5/1994 | Lee | 604/160 |
| 5,312,357 A | | 5/1994 | Bujis et al. | 604/164 |
| 5,322,513 A | * | 6/1994 | Walker | 604/161 |
| 5,328,480 A | | 7/1994 | Melker et al. | 604/164 |
| 5,356,388 A | | 10/1994 | Sepetka et al. | 604/164 |
| 5,357,955 A | | 10/1994 | Wolf et al. | 128/634 |
| 5,380,290 A | | 1/1995 | Makower et al. | 604/164 |
| 5,389,077 A | | 2/1995 | Melinyshyn et al. | 604/117 |
| 5,395,335 A | | 3/1995 | Jang | 604/102 |
| 5,407,432 A | | 4/1995 | Solar | 604/164 |
| 5,409,461 A | | 4/1995 | Steinman | 604/110 |
| 5,409,469 A | | 4/1995 | Schaerf | 604/282 |
| 5,441,481 A | | 8/1995 | Mishra et al. | 604/29 |
| 5,522,400 A | * | 6/1996 | Williams | 600/585 |
| 5,542,936 A | | 8/1996 | Razi | 604/264 |
| 5,585,013 A | | 12/1996 | Truty | 219/69.12 |
| 5,599,345 A | | 2/1997 | Edwards et al. | 606/41 |
| 5,651,767 A | | 7/1997 | Schulman et al. | 604/8 |
| 5,654,539 A | | 8/1997 | Borgos et al. | 250/227.11 |
| 5,687,727 A | * | 11/1997 | Kraus et al. | 600/434 |
| 5,728,132 A | | 3/1998 | Van Tassel et al. | 606/213 |
| 5,779,665 A | | 7/1998 | Mastrototaro et al. | 604/51 |
| 5,858,007 A | | 1/1999 | Fagan et al. | 604/256 |
| 5,891,100 A | | 4/1999 | Fleckenstein | 604/175 |
| 5,951,518 A | | 9/1999 | Licata et al. | 604/161 |
| 5,957,912 A | | 9/1999 | Heitzmann | 604/533 |

* cited by examiner

INTRODUCER ELEMENT AND METHOD OF USING SAME

FIELD OF THE INVENTION

The present invention relates to medical devices, particularly to an introducer element to assist in the placement of a medical device into a body, and more particularly to an introducer element to assist in the placement of a sensor into brain tissue.

BACKGROUND OF THE INVENTION

Most medical patients require monitoring of one or more of their medical functions during hospitalization and/or during home-treatment. Chief among the concerns regarding the monitoring process is that the measurements obtained from monitoring instrumentation are as accurate as possible. In order to provide accurate measurements, however, the monitoring instrumentation must be placed at an exact location within the body, and the monitoring instrumentation must not migrate from this exact position during the monitoring process. Other concerns related to the monitoring process are that the monitoring instrumentation can be easily inserted and positioned without the need for numerous devices that could complicate the procedure, that the monitoring instrumentation is easily removable once in place, and that the entire monitoring process reduces trauma to the tissue of the patient as much as possible.

The above concerns are especially relevant with regard to a sensor that is inserted into brain tissue in order to measure characteristics of the brain, such as $O_2$, $CO_2$, pH and temperature. These sensors tend to be flexible yet fragile, and thus have proven to be difficult to initially place within brain tissue without support and to assuredly secure at a desired depth within brain tissue.

Therefore, a need exists for a device and technique that provides safe, simple and effective introduction, securing, and sealing of a medical instrument into a body. In particular, a need exists for a device and technique that provides safe, simple and effective introduction and securing of a flexible sensor into brain tissue for monitoring purposes.

SUMMARY OF THE INVENTION

The present invention provides an introducer element. Although the invention is primarily shown and described as being used to effectuate the placement of a sensor into brain tissue, it is understood that the invention has other applications as well, such as to effectuate the placement of a medical device into other areas of the body.

The introducer element includes a body that has a longitudinal axis and that is divided into first, second, third and fourth housing areas. The third housing area is connected to the first, second and fourth housing areas and is disposed between the first and fourth housing areas as well as the second and fourth housing areas.

The first housing area includes at least a first lumen, and the second housing area includes at least a second lumen. A quantity of peel-away tubing is disposed within the second lumen, wherein at least a portion of the peel-away tubing is also located outside of the second lumen, and wherein the tubing has a slit defined therein.

The first and second lumen are separate from each other in the first and second housing areas of the introducer element body but are merged to form a combined lumen within either the third or fourth housing area.

The introducer element also includes a guide/splitting tube, which is generally disposed within the first lumen, and which passes through the slit defined within the quantity of peel-away tubing. The guide/splitting tube provides a path between the first lumen and the combined lumen. The combined lumen is also defined so as to be substantially internally lined by the quantity of peel away tubing.

In an exemplary embodiment of the present invention, the first and fourth housing areas of the body are substantially coaxial with the longitudinal axis of the body, while the second housing area is offset from the longitudinal axis of the body.

The introducer element may be used in conjunction with other equipment to insert a medical instrument, such as a sensor, into an area of the body, such as brain tissue.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

Figure 1:
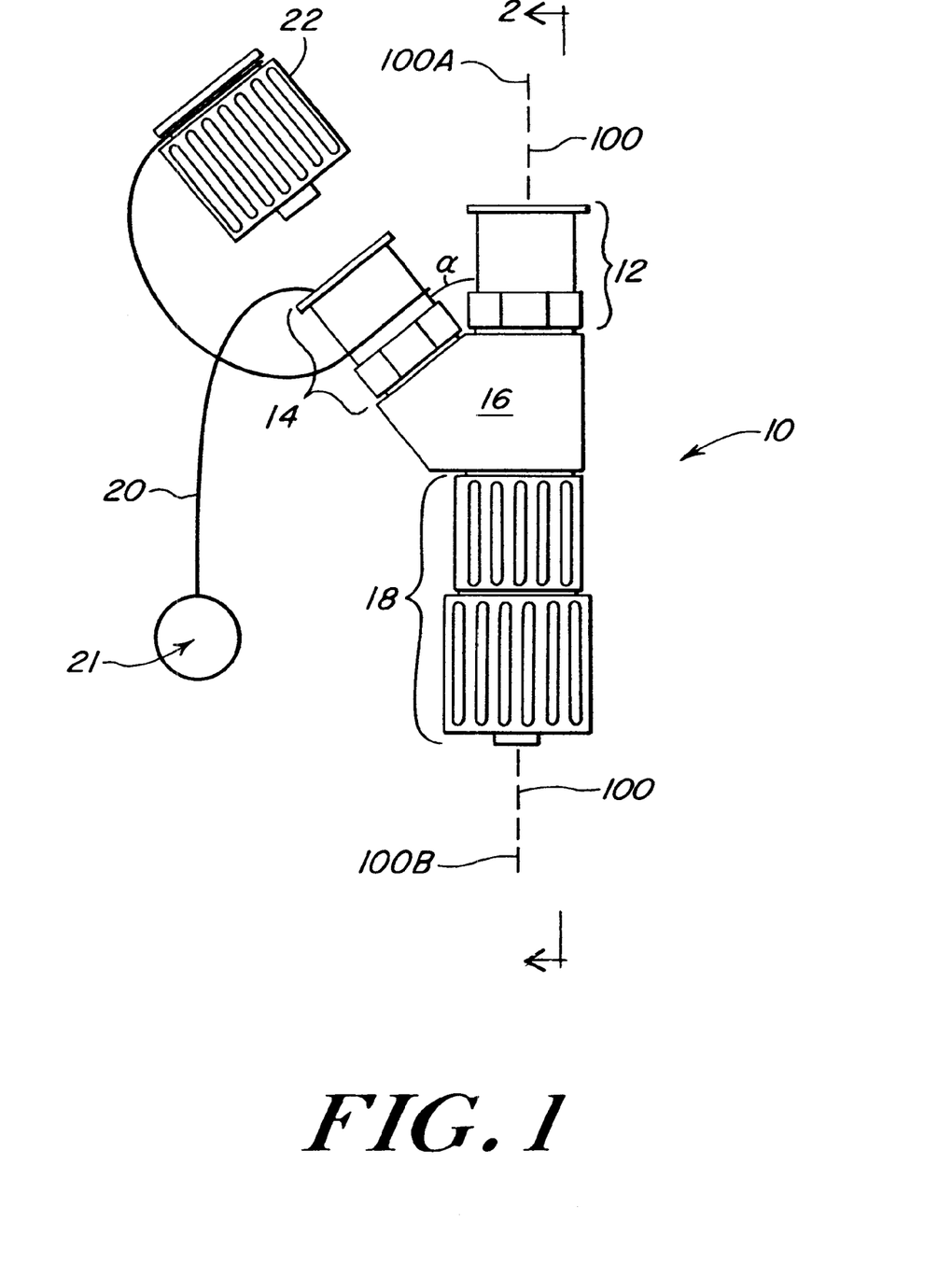
FIG. 1 is a side view of an introducer element in accordance with the present invention.

Referring initially to FIG. 1, an introducer element 10 is shown. The introducer element 10 has a body which includes first and second housing areas 12, 14, a third housing area 16, and a fourth housing area 18. The third housing area 16 is connected to the first housing area 12, the second housing area 14 and the fourth housing area 18, and is disposed between the first and fourth housing areas as well as the second and fourth housing areas.

The introducer element 10 also has a longitudinal axis 100, which has a proximal end 100A and a distal end 100B. For purposes of defining the elements of the present invention, a portion or end of an element that is described as being "proximal" is located closer to the proximal end 100A of the longitudinal axis 100 of the introducer element, while a portion or end of an element that is described as being "distal" is located closer to the distal end 100B of the longitudinal axis 100.

In an exemplary embodiment of the present invention, the first housing area 12 and the fourth housing area 18 are both substantially coaxial with the longitudinal axis 100 of the body, while the second housing area 14 is offset from the longitudinal axis of the body. In such an embodiment of the present invention, the body of the introducer element 10 will generally have a substantially "Y" shape, wherein the second housing area 14 is offset from the longitudinal axis 100 by an angle of offset (α) in the range of about 20° to 75°. One of ordinary skill in the art will ascertain, however, that the housing areas 12, 14, 16, 18 may have a wide range of positional relationships with respect to each other in addition to those described and depicted herein.

The introducer element 10 also includes a quantity of peel-away tubing 20 that is partially disposed within the element and to which a grasping element 21 is connected. The introducer element 10 can also include a cap 22 that is adapted to reversibly fit onto the second housing area 14. Both the peel-away tubing 20 and the cap 22 will be described in further detail below.

Figure 2:
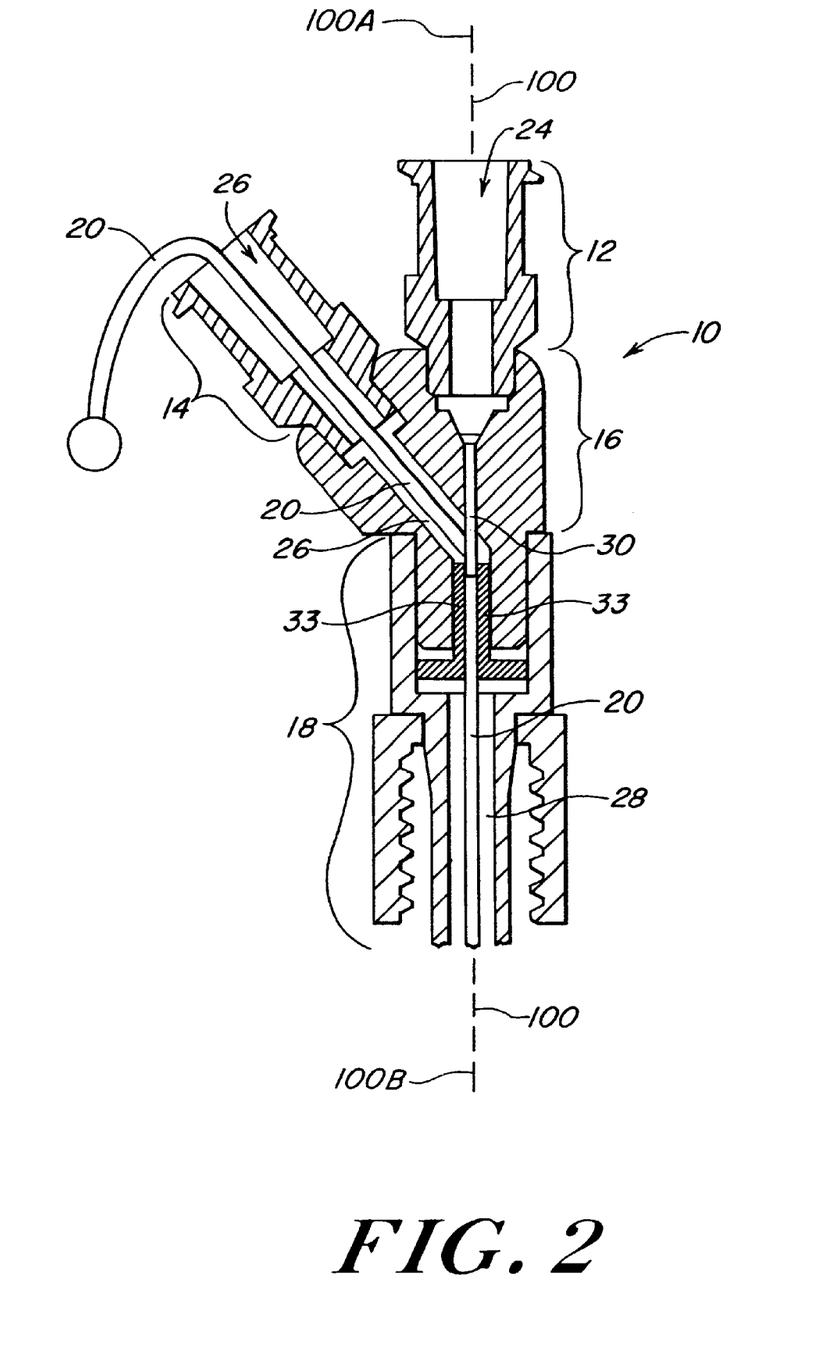
FIG. 2 is a sectional view of the introducer element of FIG. 1 taken along line 2—2 of FIG. 1.

Referring now to FIG. 2, a sectional view of the introducer element 10 of FIG. 1 is shown. The introducer element 10 includes at least two lumens defined therewithin. In the exemplary embodiment of FIG. 2, a first lumen 24 is defined within the first housing area 12, and a second lumen 26 is defined within the second housing area 14. These lumens 24, 26 are generally separated from each other in the first and second housing areas 12, 14, but merge within the either the third housing area 16 or the fourth housing area 18 of the introducer element 10 to form one combined lumen 28.

As shown in FIG. 2, the quantity of peel-away tubing 20 is partially disposed within the introducer element 10. Specifically, a portion of the tubing 20 is located outside of the second housing area 14, while the remainder of the tubing 20 is disposed within the introducer element 10 and beyond the fourth housing element 18. The tubing 20 may be made of a number of materials, including, but not limited to, polytetrafluoroethylene. Exemplary polytetrafluoroethylene tubing 20 is available from Zeus Industrial of Orangeburg, S.C. The advantages of Zeus polytetrafluoroethylene tubing will be discussed below.

Figure 3:
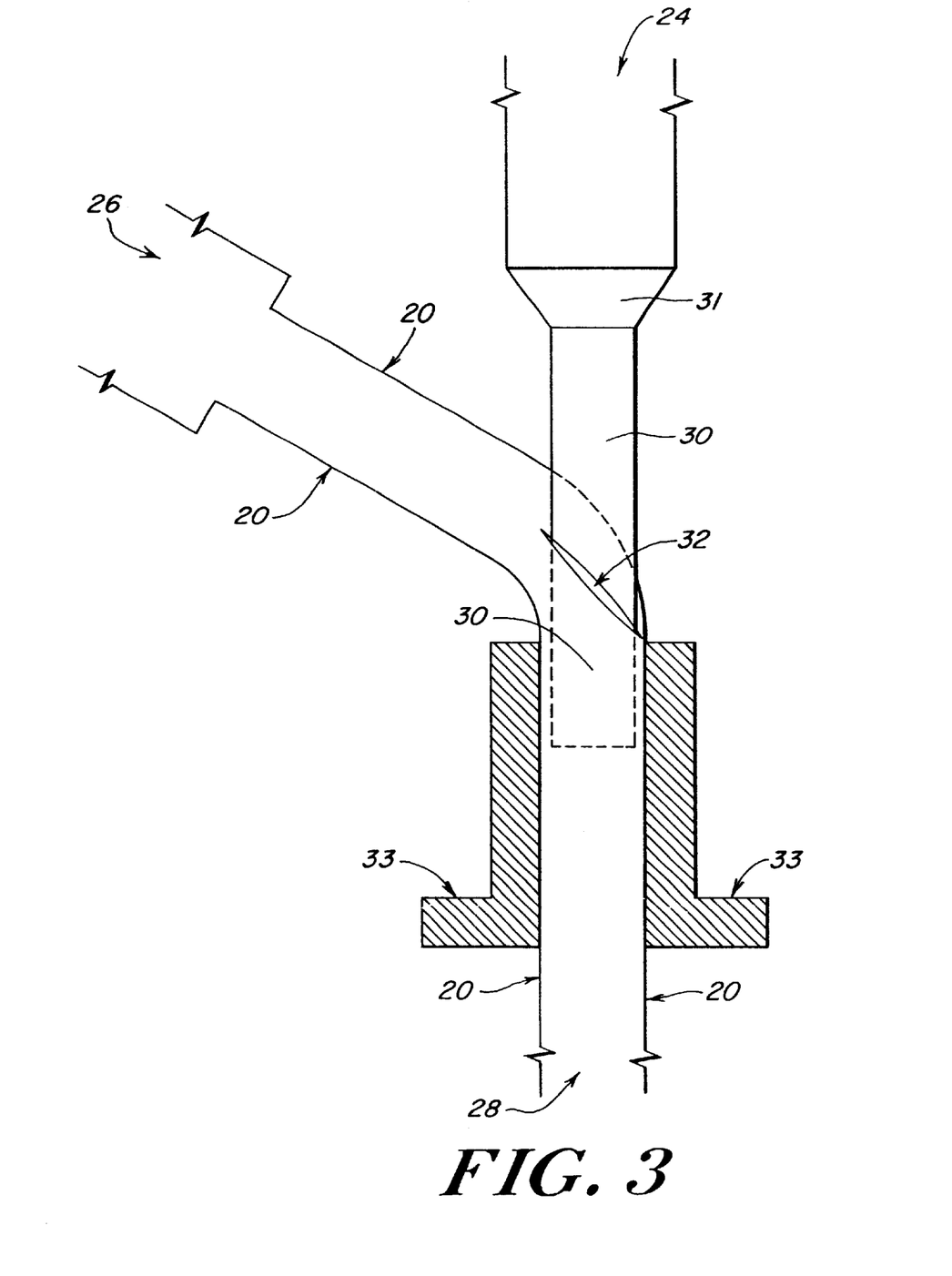
FIG. 3 is an enlarged view of a portion of the introducer element of FIG. 2.

As noted above, the first and second lumen 24, 26 of the introducer element 10 merge to form a combined lumen 28. A guide/splitting tube 30 is inserted into the first lumen 24 of the introducer element 10 and a slit 32 of the quantity of peel-away tubing 20, thus splitting the peel-away tubing, as best shown in FIG. 3. Thus, there is a continuous path defined between the first lumen 24 and the combined lumen 28. The guide/splitting tube 30 has an expanded portion 31 that is sized and shaped to keep the guide/splitting tube from sliding into the combined lumen 28 and lies flush within the third housing area 16 (as shown in FIG. 2) to permit smooth transition of introduced objects. An internal guide 33 (also shown in FIG. 2) prevents the slit 32 of the peel away tubing 20 from sliding off of the guide splitting tube 30, and also ensures the continuity of the combined lumen 28.

The introducer element 10 described above may be used in conjunction with a process (illustrated in FIGS. 4–9) for inserting a sensor into brain tissue. One of ordinary skill in the art will readily ascertain, however, that the below-described process can be utilized to assist in the insertion of other medical instruments into brain tissue and/or to assist in the insertion of a sensor or other medical instruments into other portions of the body.

Figure 4:
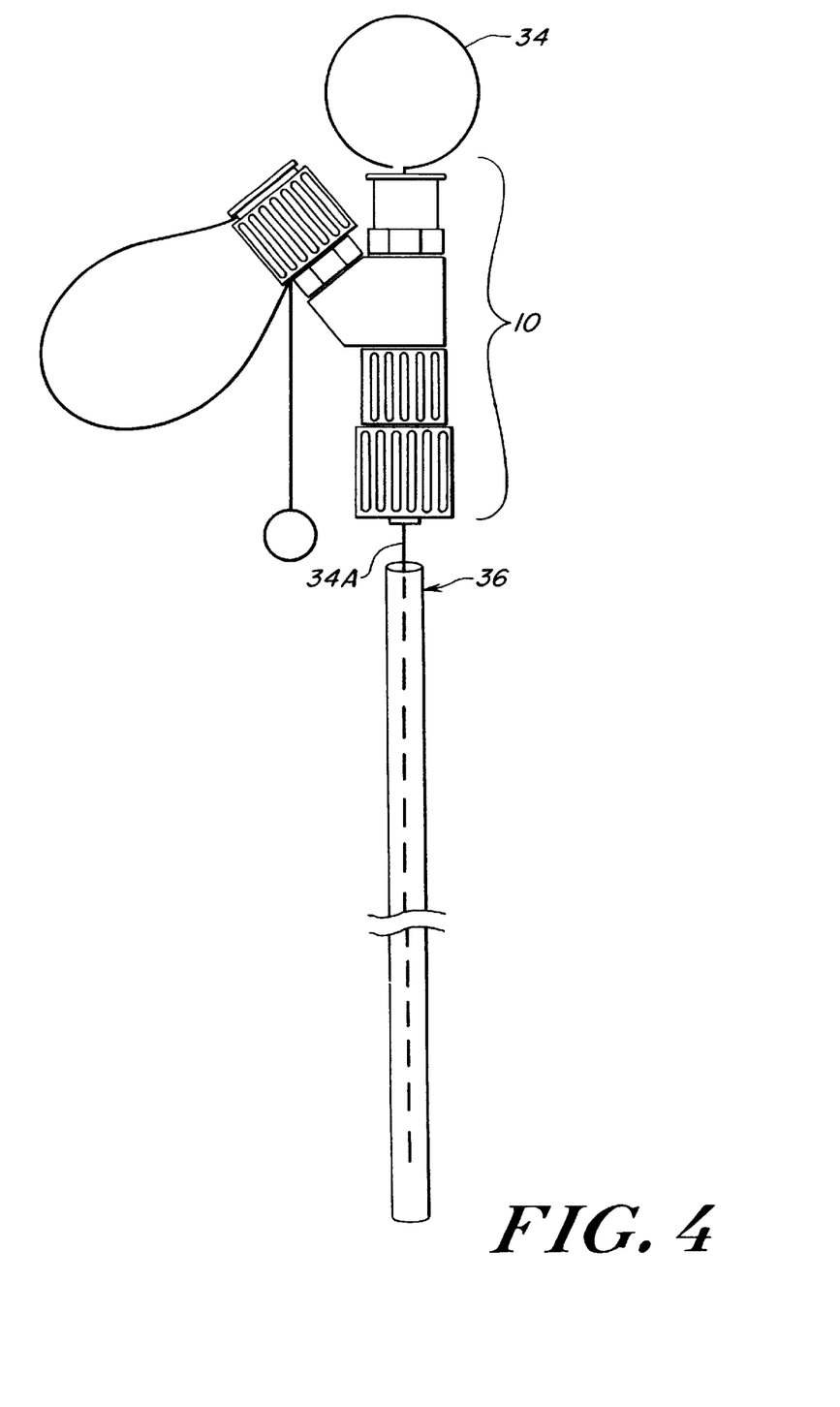
FIG. 4 is side view of the introducer element of FIG. 1 with a stylet assembled therein and with a cap reversibly secured thereto.
Figure 5:
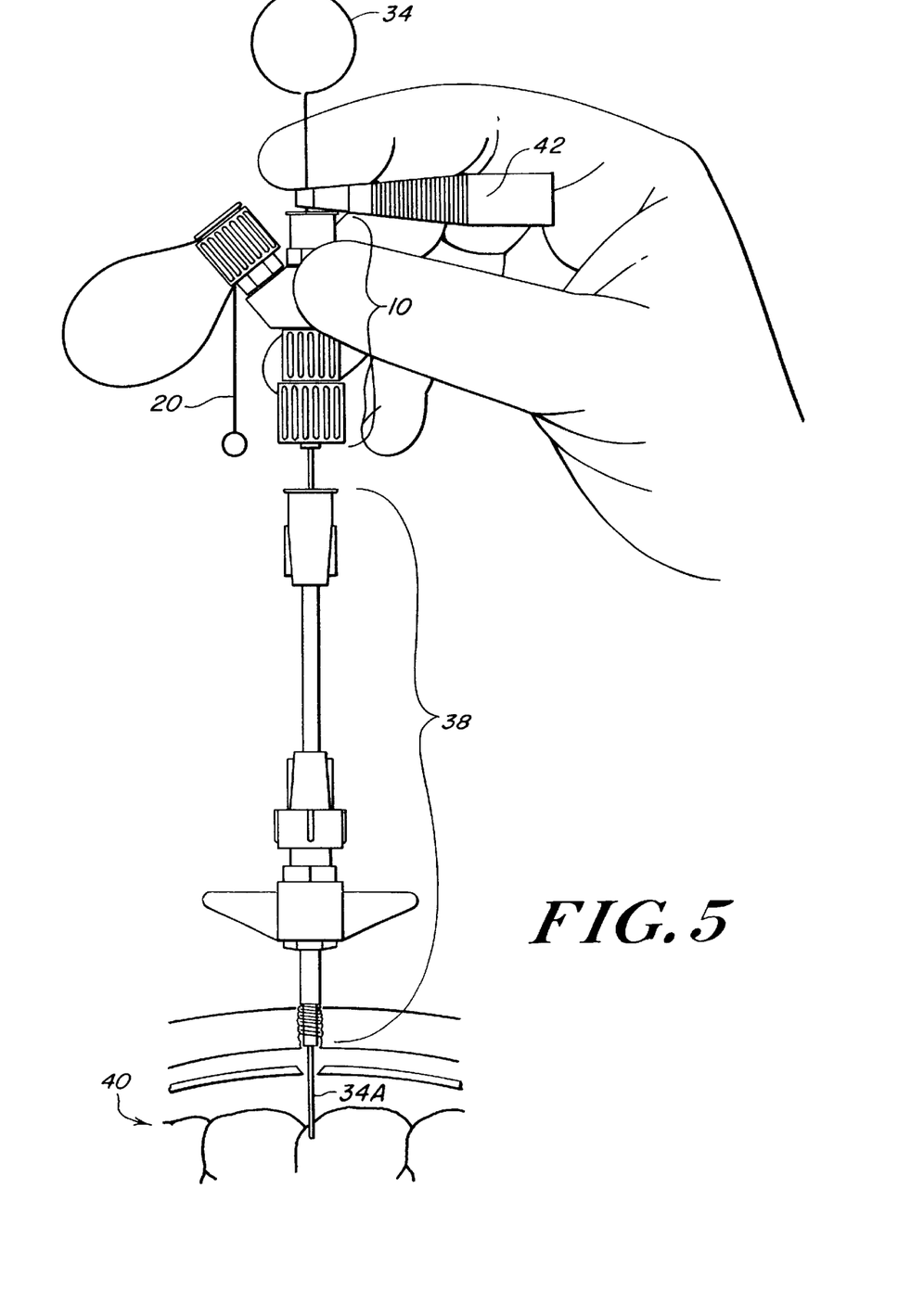
FIG. 5 is a side view of the introducer element of FIG. 1 wherein the stylet has been inserted through an entry facilitation element and into the body.

Referring now to FIG. 4, the introducer element 10 is shown with a stylet 34 having been assembled through the first lumen 24, the guide/splitting tube 30, and the combined lumen 28 (each as shown in FIGS. 2 and 3) such that at least a distally-protruding portion 34A of the stylet protrudes from the introducer element 10. This portion 34A of the stylet 34 should protrude distally beyond the distal end of the quantity of peel-away tubing. The stylet 34 and peel away tubing 20 may be enclosed by rigid protective tubing 36 in order to maintain the shape of the stylet and to provide protection to the thin walled peel away tubing. This protective tubing 36, if included, is removed from the stylet 34 to prepare the stylet for insertion into a body as shown in FIG. 5. The stylet 34 and peel-away tubing 20 lengths can be varied prior to insertion to a predetermined depth in brain tissue by the surgeon. Once a distally-protruding portion 34A (as shown in FIG. 5) of the stylet 34 and peel away tubing 20 are placed at a predetermined depth within brain tissue 40 (also as shown in FIG. 5), the stylet is secured with, for example, a clamp 42 such that the position of the stylet is maintained.

FIG. 5 depicts the introducer element 10 and stylet 34 having been inserted through an entry facilitation element 38 and into brain tissue 40. The entry facilitation element 38 provides a continuous pathway between the introducer element 10 and the brain tissue 40 to assist in the insertion of one or more medical instruments into the brain tissue. The placement, purpose and specific type of entry facilitation element 38 used in conjunction with the process may vary greatly depending on, for example, the portion of the body into which the entry facilitation element is to provide a pathway. An exemplary entry facilitation element 38 is a skull bolt that has been threaded into the skull to reach brain tissue 40 as shown in FIG. 5.

Figure 6:
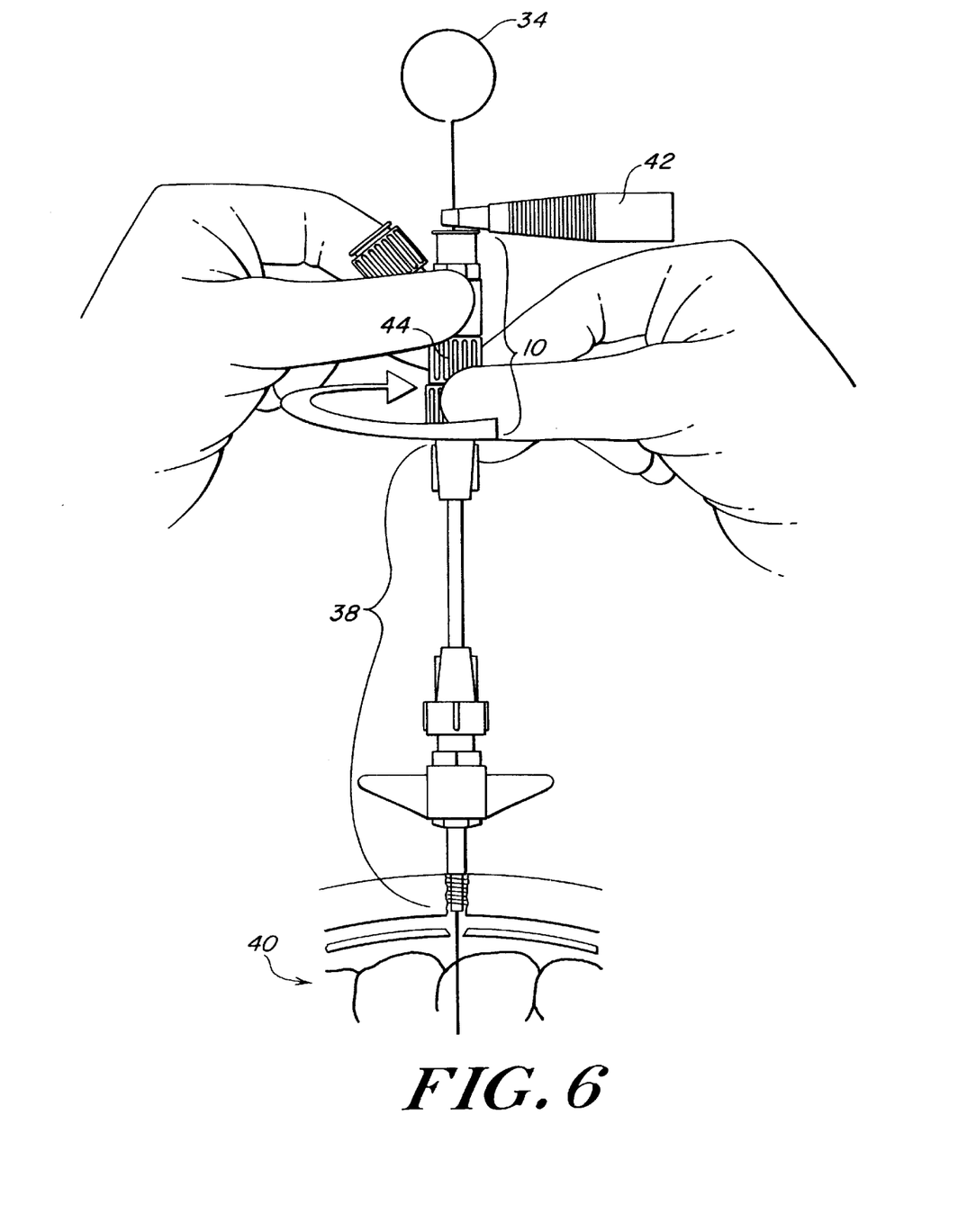
FIG. 6 is a side view of the introducer element of FIG. 1 being locked in position with respect to a body.

Then, as shown in FIG. 6, the introducer element 10 is locked in place with respect to the entry facilitation element 38. For a screw or luer type fitting, this is done by grasping the introducer element 10 and rotating a fitting 44 in the direction shown by the arrow in FIG. 6. Once the introducer element 10 is locked in place with respect to the entry facilitation element 38, both the stylet 34 and the clamp 42 may be removed while still ensuring that the quantity of peel-away tubing remains unremoved from, and undisturbed with respect to, the brain tissue 40.

Figure 7:
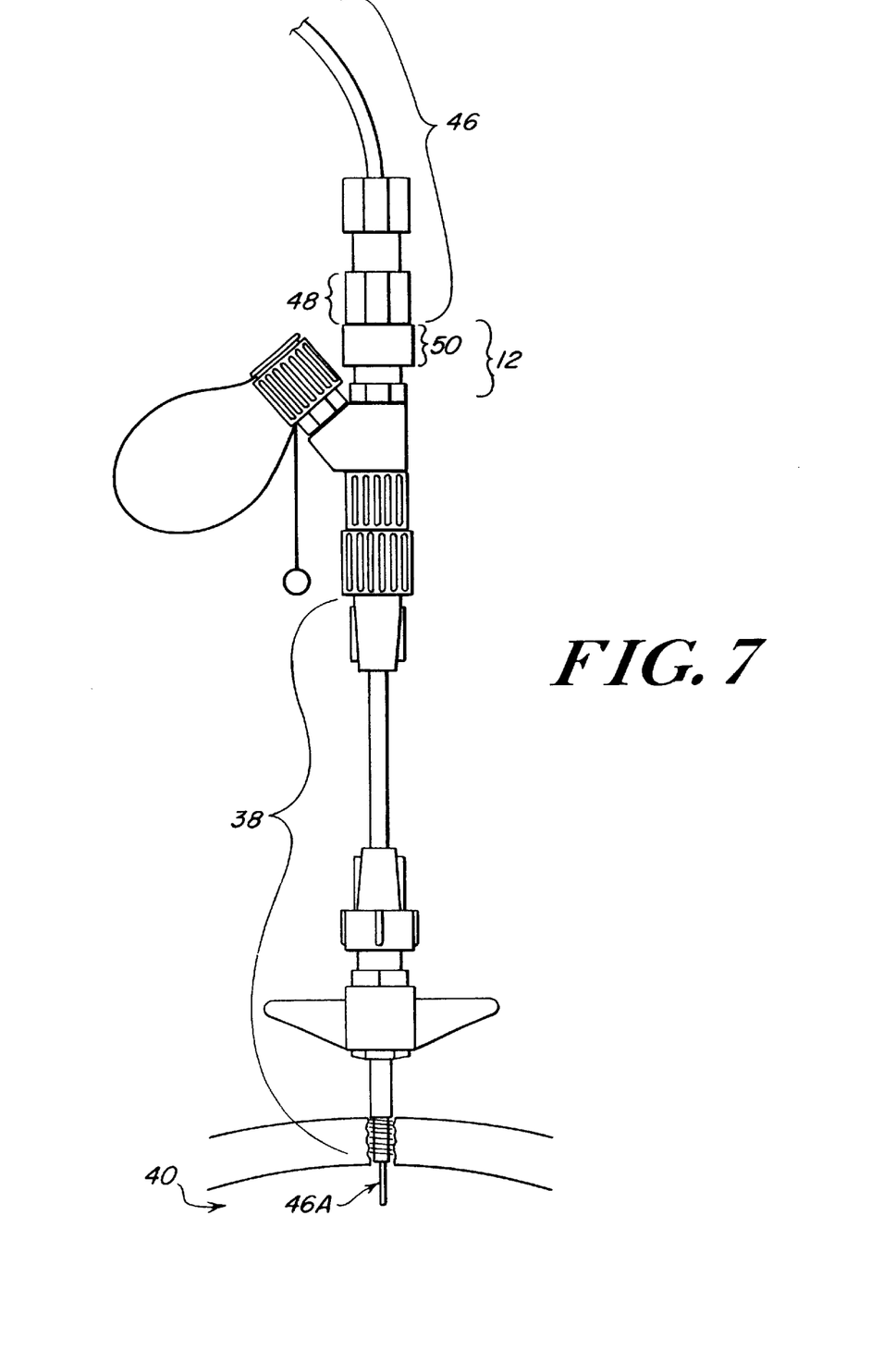
FIG. 7 is a side view of the introducer element of FIG. 1 wherein a medical instrument has been inserted into and through the introducer element, through an entry facilitation element, and into a body.

As shown in FIG. 7, a medical instrument 46, such as a sensor, is then inserted into the first housing area 12 of the element 10. The sensor 46 is connected to the introducer element 10 by the interlocking of a fitting 48 of the sensor with a fitting 50 of the first housing area 12 of the introducer element. The sensor 46 is then carefully advanced into and through the first lumen 24, the guide splitting tube 30, the and the combined lumen 28 (each as shown in FIGS. 2 and 3), and then into and through the entry facilitation element 38 until a portion 46A of the sensor reaches the predetermined depth measurement within the brain tissue 40.

Figure 8:
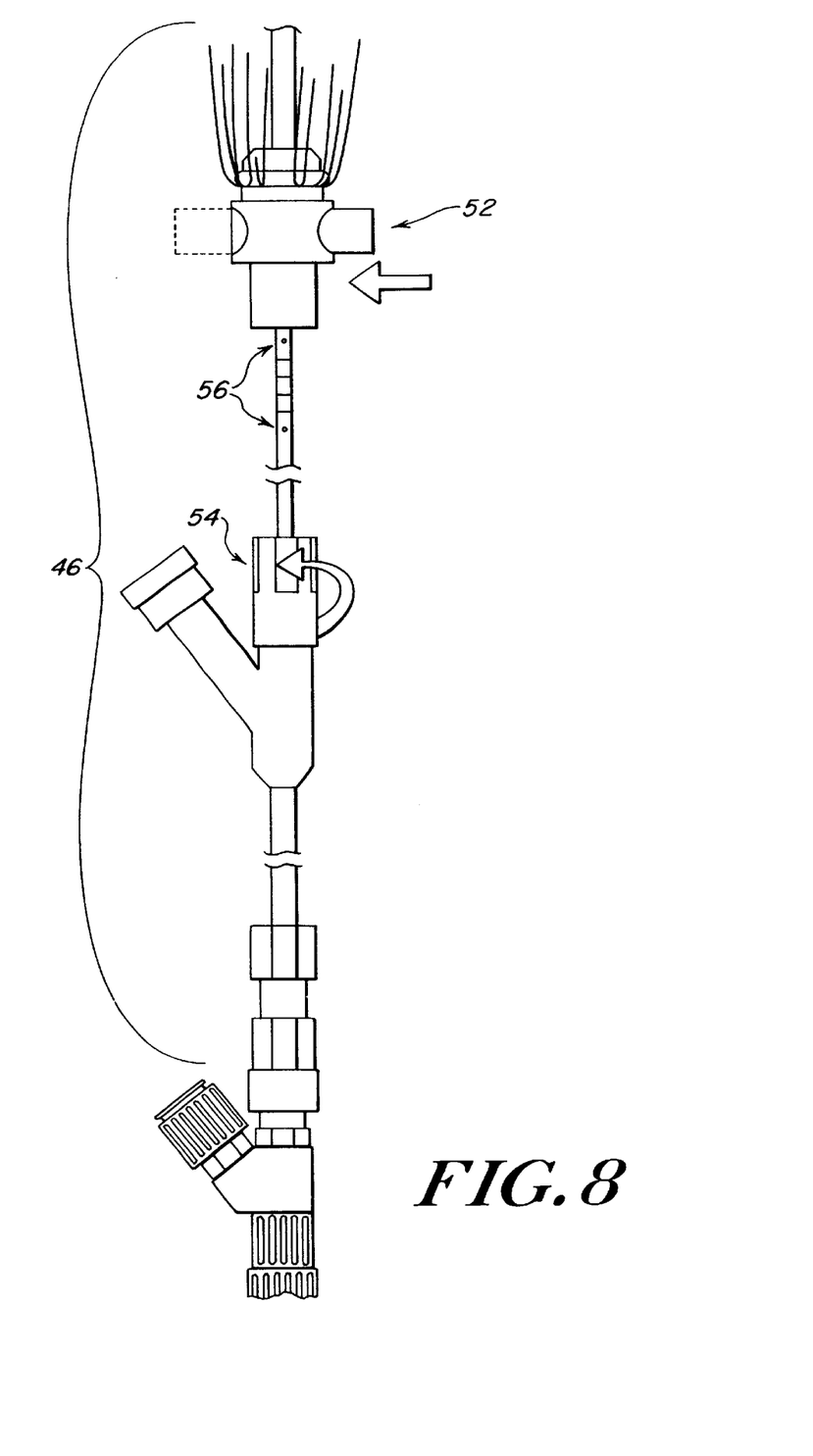
FIG. 8 is a side view of the medical instrument being locked in position with respect to the introducer element of FIG. 1.

Referring now to FIG. 8, the sensor 46 generally will include an advancement lock 52 and a rear clamp 54 wherein, once the portion 46A (as shown in FIG. 7) of the sensor has been advanced to the predetermined depth measurement within the brain tissue 40 (also as shown in FIG. 7), the advancement lock and rear clamp are both locked in order to maintain this predetermined depth measurement of the sensor. The sensor 46 may optionally include numeric indicia 56 in order to assist in and/or verify that the portion 46A of the sensor 46 has attained the predetermined depth measurement in the brain tissue.

Figures 9, 9A:
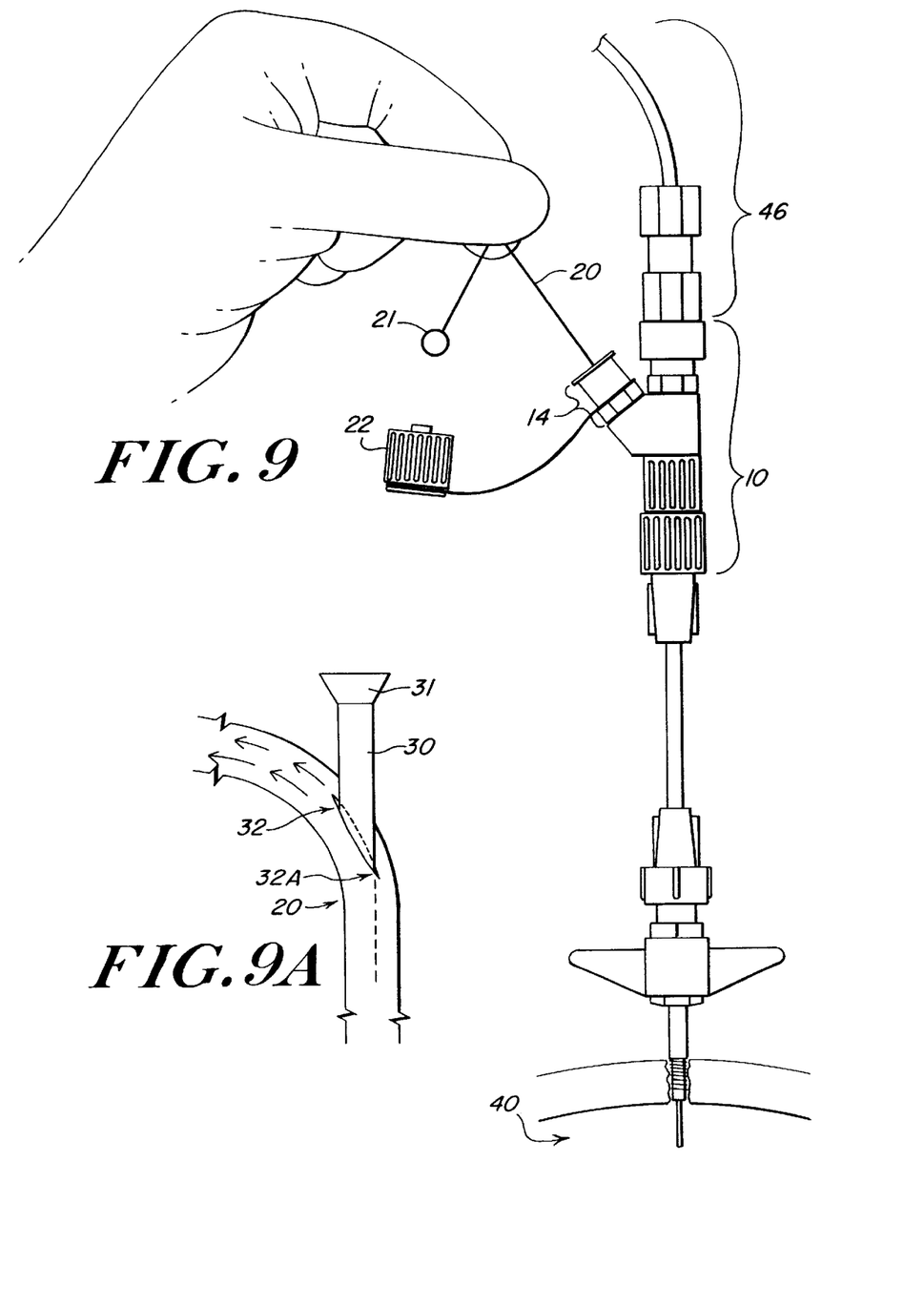
FIG. 9 is a side view of the introducer element of FIG. 1 during the removal of a quantity of peel-away tubing from the introducer element.
FIG. 9A is a view of the guide/splitting tube and peel away tubing within the introducer element of FIG. 9 during the removal of the quantity of peel away tubing from the introducer element.

Once the portion 46A of the sensor has been advanced into the brain tissue 40 within the peel away tubing 20, and the sensor has been locked in place, the quantity of peel-away tubing is removed from the introducer element 10 as shown in FIGS. 9 and 9A. Specifically, the cap 22 is removed from the second housing area 14 and then the grasping element 21 is pulled to withdraw the peel-away tubing 20. In this instance, the grasping element 21 is pulled with enough force (at least approximately 0.04 pounds) such that the tubing splits at its slit, as best shown in FIG. 9A.

FIG. 9A depicts the quantity of peel-away tubing 20 contained in the introducer element 10 of FIG. 9 while the tubing is being pulled in the direction indicated by the double arrows in FIG. 9A. When the tubing 20 is pulled in such a direction with the requisite amount of force, a rear portion 32A of the slit will be forced against the guide/splitting element and the slit will propagate. In an embodiment wherein Zeus Industrial tubing 20 is used, the slit 32 will propagate axially as shown by the dashed lines in FIG. 9A. This is because the Zeus Industrial tubing is manufactured such that its molecular chains are aligned. This molecular arrangement ensures that if the tubing 20 includes a slit 32, and the tubing is pulled such that the tubing begins to rip at this slit (as caused by the rear portion 32A of the slit contacting the guide/splitting tube 30), the tubing will continue to split axially from that slit. Thus, if Zeus Industrial tubing is used, the tubing 20 removal process can likely occur without interruption and without the threat that the tubing will not completely, uniformly tear and/or will not be completely removed from the introducer element 10.

The pulling force is continued until the tubing 20 is completely removed from the introducer element 10. Once the tubing 20 is removed, the sensor can actively sense brain tissue 40 characteristics.

The introducer element 10 and its components may have a variety of shapes and sizes in accordance with the present invention. For example, the combined lumen 28 should be sized such that it may accept many different medical instruments, especially those that have a diameter of approximately 0.1 millimeters to approximately 2.5 millimeters. The quantity of peel-away tubing 20 generally will have a length of between about 9.0 inches and about 10.5 inches, with a length of about 9.6 inches to 10.0 inches being preferred. The peel-away tubing 20 also will generally have a wall thickness of between about 0.0127 millimeters and 0.0635 millimeters, with a wall thickness of about 0.0254 millimeters to 0.0508 millimeters being preferred. The tubing 20 also has an inner diameter of about 0.381 millimeters to 0.889 millimeters, with an inner diameter of about 0.508 millimeters to about 0.762 millimeters being preferred. Of course, tubing diameter will vary in relation to the diameter of the medical instrument to be inserted within the tubing.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An introducer element, comprising:
   a body having a first and second lumen, each having a distal end and a proximal end, wherein the first and second lumen merge at their distal ends to provide a combined lumen having a proximal end and a distal end;
   a quantity of tearable, selectively removable peel-away tubing having a proximal end and a distal end, wherein a slit is defined at a point between the proximal end and the distal end of the quantity of peel away tubing, the quantity of peel-away tubing being disposed within the second lumen and the combined lumen; and
   a tube disposed within the first lumen, passing through the slit defined by the quantity of peel-away tubing and into the combined lumen.

2. The introducer element of claim 1, wherein the tube provides a continuous path between the first lumen and the combined lumen.

3. The introducer element of claim 2, wherein the proximal end of the quantity of peel-away tubing extends from a proximal end of the second lumen and the distal end of the quantity of peel-away tubing extends from the distal end of the combined lumen.

4. The introducer element of claim 3, further comprising a grasping element secured to the proximal end of the quantity of peel-away tubing.

5. The introducer element of claim 1, wherein the quantity of peel-away tubing is made of polytetrafluoroethylene.

6. An introducer element, comprising:
   a body having a longitudinal axis and including first, second, third and fourth housing areas, the third housing area being connected to the first, second and fourth housing areas and being disposed between the first housing area and fourth housing area and between the second housing area and fourth housing area, the first housing area having a first lumen defined therewithin, the first lumen having a proximal end and a distal end, the second housing area having a second lumen defined therewithin, the second lumen having a proximal end and a distal end, wherein the first lumen and the second lumen merge at their distal ends to provide a combined lumen;
   a quantity of tearable, selectively removable peel-away tubing having a proximal end and a distal end, wherein a slit is defined at a point between the proximal end and the distal end of the quantity of peel away tubing, the quantity of peel-away tubing being disposed within the second lumen and the combined lumen; and
   a tube disposed within the first lumen, passing through the slit defined by the quantity of peel-away tubing and into the combined lumen.

7. The introducer element of claim 6, wherein the first housing area is substantially coaxial with the longitudinal axis of the body.

8. The introducer element of claim 6, wherein the fourth housing area is substantially coaxial with the longitudinal axis of the body.

9. The introducer element of claim 6, wherein the second housing area is offset from the longitudinal axis of the body.

10. The introducer element of claim 9, wherein the second housing area is offset from the longitudinal axis of the body by an angle in the range of about 20° to 75°.

11. The introducer element of claim 6, wherein the quantity of peel-away tubing is made of polytetrafluoroethylene.

12. The introducer element of claim 6, further comprising a grasping element secured to the proximal end of the quantity of peel-away tubing.

13. A method for introducing a medical instrument into a body, comprising the steps of:
   providing an introducer element, comprising:
      a body having a first and second lumen, each having a distal end and a proximal end, wherein the first and second lumen merge at their distal ends to provide a combined lumen having a proximal end and a distal end;

a quantity of tearable, peel-away tubing having a proximal end and a distal end, wherein a slit is defined at a point between the proximal end and the distal end of the quantity of peel away tubing, the quantity of peel-away tubing being disposed within the second lumen and the combined lumen;

a tube disposed within the first lumen, passing through the slit defined by the quantity of peel-away tubing and into the combined lumen; and a stylet disposed within the introducer element such that at least a portion of the stylet distally protrudes from the combined lumen of the introducer element;

providing an entry facilitation element having at least one lumen defined therethrough;

inserting the entry facilitation element into the body to a predetermined depth within the body such that at least a portion of the entry facilitation element protrudes from the body;

properly placing the introducer element in the entry facilitation element;

removing the quantity of peel-away tubing from the introducer element.

14. The method of claim 13, wherein the step of properly placing the introducer element in the entry facilitation element comprises the steps of:

inserting the distally protruding portion of the stylet into and through one of the at least one lumen of the entry facilitation element and into the body to a predetermined depth within the body;

securing the stylet;

securing the introducer element to the entry facilitation element;

unsecuring the stylet; and removing the stylet from the body, the entry facilitation element and the introducer element.

* * * * *